United States Patent [19]

Murch et al.

[11] 3,933,738

[45] Jan. 20, 1976

[54] FLAME RETARDANT ADDUCT OF CYCLOPHOSPHONITRILIC CHLORIDE AND HEXAMETHYLPHOSPHORAMIDE

[75] Inventors: Robert M. Murch, Ashton; Eldon E. Stahly, Ellicott City, both of Md.

[73] Assignee: The United States of America as represented by the Secretary of the Navy, Washington, D.C.

[22] Filed: May 23, 1975

[21] Appl. No.: 580,451

Related U.S. Application Data

[63] Continuation-in-part of Ser. No. 436,779, Jan. 25, 1974, abandoned.

[52] U.S. Cl. ..................... 260/45.9 NP; 260/551 P
[51] Int. Cl.² ............................................. C08J 3/20
[58] Field of Search ................. 260/45.9 NP, 551 P

[56] References Cited

UNITED STATES PATENTS

| | | | |
|---|---|---|---|
| 2,786,075 | 3/1957 | Krase et al. | 260/551 P |
| 3,131,207 | 4/1964 | Ratz | 260/927 |

*Primary Examiner*—V. P. Hoke
*Attorney, Agent, or Firm*—R. S. Sciascia; Arthur L. Branning; T. McDonnell

[57] ABSTRACT

The adduct of hexamethylphosphoramide and a cyclophosphonitrilic chloride, $(PNCl_2)_n \cdot [(CH_3)_2N]_3PO$, useful for enhancing the fire retardancy of epoxy resins and a method for enhancing the fire retardancy of epoxy resins through the combination therewith.

6 Claims, No Drawings

3,933,738

FLAME RETARDANT ADDUCT OF CYCLOPHOSPHONITRILIC CHLORIDE AND HEXAMETHYLPHOSPHORAMIDE

CROSS-REFERENCE TO RELATED APPLICATION

This is a continuation-in-part of application Ser. No. 436,779 filed Jan. 25, 1974 now abandoned.

BACKGROUND OF THE INVENTION

The invention relates to epoxy resins containing a fire retardant additve as well as a method by which epoxy resins are rendered fire retardant. Epoxy resins are widely accepted as useful products for a variety of purposes because epoxies are so versatile. By versatile is meant that epoxies vary in molecular weight, viscosity, surface properties and curing properties. Some are high molecular weight, high melting solids while others are low molecular weight liquids. By selecting the proper curing agent they can be made to cure quickly and slowly, at room temperature or at elevated temperatures. Epoxy resins can be used where a soft flexible material is required or where a hard, tough material is required. Epoxies provide excellent electrical insulating properties as well as a high resistance to corrosive media. Perhaps, though, epoxy resins most well known property is that of adhesion.

Epoxy resins, however, like many resins are not by themselves resistant to fire. To render them fire retardant, additives must be blended with the epoxy. The desirability of rendering epoxy resins fire resistant is evident. It is especially important that epoxies be rendered resistant to fire when used as an insulating compound to embed electrical equipment. Epoxies are also used as adhesives in equipment that undergo great changes in temperature and pressure where fire is likely to occur. It is essential that the epoxy resin be fire retardant to reduce the likelihood of fire.

SUMMARY OF THE INVENTION

Accordingly, it is an object of the invention to provide an epoxy composition that is fire retardant.

Another object of the invention is to provide an adduct that when added to an epoxy resin will enhance the fire retardancy of that epoxy resin.

Still another object of the invention is to provide a method of enhancing the fire retardancy of an epoxy resin.

And yet another object of the invention is to provide fire retardant additives for epoxy resins which give minimum interference with the properties of the resins.

These and other objects are achieved by the inclusion of the adduct of hexamethylphosphoramide and a cyclophosphonitrilic chloride in an epoxy resin.

DETAILED DESCRIPTION

By "fire retardancy" is meant that the resin is resistant to flame after the igniting flame has been removed. In other words, the fire retardant epoxy resin will not support combustion by itself. When in contact with an open flame, however, it may become charred.

The fire retardancy enhancing additives of this invention are best produced by admixing at room temperature for at least about 10 minutes but preferably for 20 minutes in a mole ratio of 1:1 hexamethylphosphoramide, $[(CH_3)_2N]_3PO$, and a cyclophosphonitrilic. In order to facilitate the removal of the final product from the reaction vessel, an excess of hexamethylphosphoramide or an inert diluent such as benzene is used, thereby the product is in a slurry upon completion of the reaction. Preferably the cyclophosphonitrilic is either hexachlorocyclotriphosphonitrile, $(PNCl_2)_3$ or octachlorocyclotetraphosphonitrile $(PNCl_2)_4$ or a mixture of the two.

The above reaction produces an adduct of the reactants which is a complex of the two molecules. The formulas for the two preferred adducts is $(PNCl_2)_n \cdot [(CH_3)_2N]_3PO$ where $n = 3$ or $4$.

The types of epoxy resins contemplated to be used are the epoxy resins produced by Shell Oil Company under the trademark EPON. Such resins are of two types. The first type is derived from the diglycidyl ether of Bisphenol-A and may be modified with monoepoxy diluents. These epoxies have the general formula

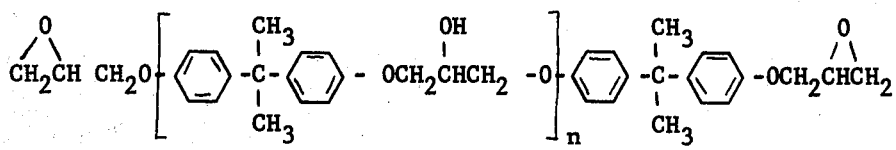

and are reaction products of epichlorohydrin and bisphenol-A.

The second type of epoxy resin is derived from a multiglycidyl derivative of a novolac. An example of such a resin is one having the following formula

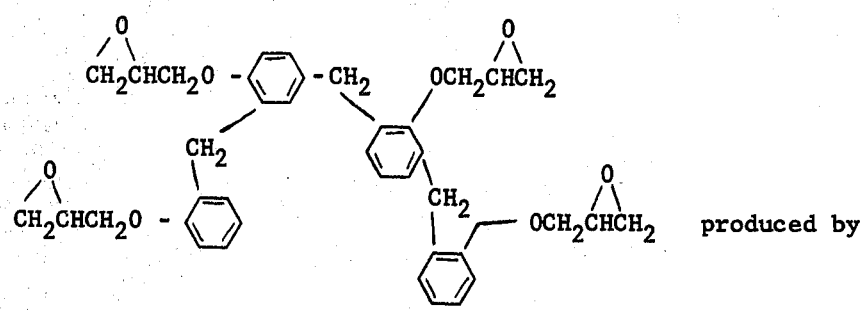

produced by reacting phenol and formaldehyde.

A listing of the EPON resins to which the adduct of the invention may be added may be found in *Handbook of Epoxy Resins*, Lee and Neville, 4–66, McGraw-Hill Book Company, 1967. The use herein of EPON resins is merely meant to be illustrative and not a limitation of the specific epoxy resin which may be utilized within the scope of the invention. It is understood that epoxy resins derived from the diglycidyl ether of bisphenol-A or a multiglycidyl derivative of a novolac can be used in the context of the present invention; even though not an EPON resin.

The epoxy resin may be cured with any known curing agent. Those proven to be useful as curing agents are those derived from the amines, primary, secondary and tertiary, as well as Lewis Acids and acid anhydrides. Table I is provided as an example of known curing agents for epoxy resins. While it is quite common to cure an epoxy resin at room temperature the curing step is hastened if the resin is heated above room temperature of 70°C. Table I lists preferred temperature range for each curing agent.

TABLE I

| Curing Agent | Chemical Type | Concentration parts/hundred parts of resin | Curing temperature °F |
|---|---|---|---|
| Diethylentriamine | Polyamine | 10–12 | 60–300 |
| Triethylentetriamine | Polyamine | 11–13 | 60–300 |
| Diethylaminopropylamine | Polyamine | 4–8 | 77–300 |
| N-Amioethylpiperozine | Polyamine | 20–23 | 80–300 |
| M-Phenylenediamine | Polyamine | 13–14 | 140–400 |
| Methylene Dianiline | Polyamine | 28–30 | 140–400 |
| Diaminodiphenyl Sulfone | Polyamine | 20–30 | 240–400 |
| $BF_3$Monoethylamine | Lewis Acid Amino Complex | 2–4 | 240–400 |
| Dodecenylsuccinic Anhydride | Anhydride | 85–95 | 175–500 |
| Phythalic Anhydride | Anhydride | 70–80 | 200–300 |
| Hexalhydrophtalid Anhydride | Anhydride | 75–85 | 200–400 |
| Chlorendic Anhydride | Anhydride | 100–120 | 200–400 |
| Trinellectic Anhydride | Anhydride | 30–40 | 210–400 |
| Tetrahydrophydralic Anhydride | Anhydride | 75–80 | 200–300 |

Fire retardance according to the novel aspects of the invention may be achieved in two ways. The first is by mixing hexamethylphosphoramide, a cyclophosphonitrilic chloride, a curing agent and an epoxy resin and heating to cure the mixture. In the second, a stoichiometric amount of hexamethylphosphoramide may be reacted with the cyclophosphonitrilic chloride and then the adduct of such a reaction is added to the epoxy resin along with a curing agent. The mixture is then cured by heating. The latter method is preferred.

Generally it has been found that by mixing from 1 to 30% by weight of the adduct with the epoxy resin, the fire retardancy properties of the resin is enhanced. A preferred range is from 5 to 20% by weight of the adduct.

In order to more fully illustrate the advantages and new features of the invention the following examples are presented.

EXAMPLE I

Hexamethylphosphoramide, 1.0 g and hexachlorocyclotriphosphonitrile $(PNCl_2)_3$, 0.7 g, and allyl glycidyl ether, 1.0 g, were mixed, then stirred into 7.0 g of a general purpose epoxy casting resin (Bisphenol-A, epichlorohydrin polymer), EPON 828. After complete mixing, methylene dianiline, 3.0 g, was added and this mixture was heated at 90°C for 1 hour. The oxygen index of this resin was substantially higher (0.31) than would be expected from a similar loading of the phosphonitrilic chloride to the epoxy alone.

EXAMPLE II

Hexamethylphosphoramide, 1.0 g, allyl glycidyl ether, 1.0 g, and hexachlorocyclotriphosphonitrile, 1.0 g, were mixed and heated to 90°C until a clear mixture was formed. After cooling to approximately 50°C the mixture was added to EPON 828, 7.0 g, and methylene dianiline, 3.0 g. The resin was heated to 90°C for 90 minutes then at 120°C for 2 hours. The oxygen index of this resin was greater than 0.30.

EXAMPLE III

A resin was prepared using the technique described in Example I except that the hexamethylphosphoramide was omitted. The oxygen index was 0.26.

EXAMPLE IV

A resin was prepared from an epoxy-Novolac type resin (Shell EPON 154), 30.0 g, hexamethylphosphoramide, 3.0 g, hexachlorocyclotriphosphonitrile, 3.0 g, pentaerythritol tetrakis mercaptopropionate, 9.0 g, and methylenedianiline, 3.0 g. This mixture was thoroughly stirred, then heated at 90°C for 2 hours and at 125°C for 4 hours. The cured resin had an oxygen index of 0.29.

EXAMPLE V

Hexachlorocyclotriphosphonitrile, 11 g, was stirred with hexamethylphosphoramide, 17.0 g, in a reaction vessel and their admixture caused an exotherm that heated the mixture to 40°C. This adduct, a solid that melts at about 40°C, was used with Shell EPON 154 or EPON 828 to produce resins with oxygen index values of 0.32 for the former and 0.34 for the latter.

EXAMPLE VI

A 6 inch × 6 inch plaque was prepared by saturating six layers of chopped glass mat with a resin consisting of 96 g of EPON 828, 12 g of hexamethylphosphoramide, 12 g of hexachlorocyclotriphosphonitrile, 12 g of allylglycidyl ether and 36 g of methylene dianiline. The composite was held at 50°C for 1 hour, at 100°C for 4 hours and 150°C for 18 hours. The cured laminate has an oxygen index of 0.34.

In the Examples the oxygen index was obtained by using the method disclosed under ASTM D 2863-70. By "oxygen index" is meant the minimum oxygen concentration, expressed in volume percent, in a mixture of oxygen and nitrogen that will just support combustion of a material under the conditions of the method. Accordingly, a material having a high oxygen index requires more oxygen to support combustion and is therefore, more fire retardant than one having a low oxygen index.

Examples I and II when compared to Example III illustrate that the adduct of hexamethylphosphoramide and hexachlorocyclotriphosphonitrile yields a resin more fire retardant than one containing only hexamethylphosphoramide as a fire retardant agent. Example V illustrates that it is preferable to react hexamethylphosphoramide and the hexachlorocyclotriphosphonitrile to form the adduct and then add that adduct to the epoxy rather than merely adding the reactants to the epoxy resin before they have reacted to form the adduct.

It is further to be noted that the oxygen index of the epoxy resins used in the examples is approximately 0.19. It is apparent then that the use of the adduct of the invention significantly increases the fire retardancy of the resin.

EXAMPLE VII

Hexamethylphosphoramide, 17.95 g and a mixture of hexa-and octa-chlorocyclotriphosphonitrile in a hexa-to-octa ratio of 4:1, 34.8 g in 150 ml of benzene were mixed for two hours at 80°C, then heated at 150°C at 0.1 mm Hg in order to eliminate all excess liquids. A viscous substance remained. This substance was added to EPON 828 and the epoxy cured. The oxygen index of this resin was 0.34.

Obviously many modifications and variations of the present invention are possible in light of the above teachings. It is therefore to be understood that within the scope of the appended claims the invention may be practiced otherwise than as specifically described.

What is claimed and desired to be secured by letters patent of the United States is:

1. An epoxy resin having enhanced fire retardancy properties which comprises an epoxy resin and an additive selected from the class consisting of $(PNCl_2)_3 \cdot [(CH_3)_2N]_3PO$, $(PNCl_2)_3 \cdot [(CH_3)_2N]_3PO$, and mixtures thereof in a flame retardant amount.

2. The epoxy resin of claim 1 wherein said compound constitutes from 1 to 30 mole percent of the total weight.

3. The epoxy resin of claim 1 wherein said compound constitutes from 5 to 20 mole percent of the weight.

4. A method for enhancing the fire retardancy characteristics of epoxy resins which comprise admixing an additive selected from the class consisting of $(PNCl_2)_3 \cdot [(CH_3)_2N]_3PO$, $(PNCl_2)_3 \cdot [(CH_3)_2N]_3PO$, and mixtures thereof in an amount from about 1 to about 30 mole percent of the combined weight with an uncured epoxy resin and curing said epoxy resin.

5. The method of claim 4 wherein from 5 to 20 mole percent of said additive of claim 1 is added.

6. A method for enhancing the fire retardancy characteristic of epoxy resins which comprises admixing in a 1:1 mole ratio hexamethylphosphoramide and a cyclophosphonitrilic chloride selected from the class consisting of hexachlorocyclotriphosphonitrile, octachlorocyclotetraphosphonitrile, and mixtures thereof with an uncured epoxy resin; and curing said epoxy resin.

* * * * *